US005513648A

United States Patent [19]
Jackson

[11] Patent Number: 5,513,648
[45] Date of Patent: May 7, 1996

[54] PARTIAL BODY PLETHYSMOGRAPH FOR MEASURING HUMAN RESPIRATORY SYSTEM IMPEDANCE

[75] Inventor: Andrew C. Jackson, Brookline, Mass.

[73] Assignee: Trustees of Boston University, Boston, Mass.

[21] Appl. No.: 202,660

[22] Filed: Feb. 28, 1994

[51] Int. Cl.$^6$ .................................................. A61B 5/08
[52] U.S. Cl. ................................. 128/721; 128/716
[58] Field of Search ............................ 128/721, 713, 128/734, 720, 716, 693, 719, 633, 724, 686, 688, 719, 713, 720, 721, 729, 693; 600/21; 248/393, 229; 297/313

[56] References Cited

U.S. PATENT DOCUMENTS

| | | | |
|---|---|---|---|
| 4,448,454 | 5/1984 | Scott | 297/313 |
| 5,323,994 | 6/1994 | Shillington et al. | 248/229 |

OTHER PUBLICATIONS

"Respiratory Transfer Impedance between 8 And 348 Hz In Guinea Pigs Before And After Bronchial Challenge," Jamil F. Sobh, Boston University, 1993, 64 pages excluding Appendices.
"Design And Clinical Use Of A Partial Body Plethysmograph For Measuring Transfer Impedance In Humans," Frederic T. Arbogast, Boston University, 1993, 77 pages excluding Appendices A–C.
"Total Respiratory Input and Transfer Impedances in Humans", R. Peslin et al., *American Physiological Society*, 1985, pp. 492–501.
"Reliability of Parameter Estimates From Models Applied to Respiratory Impedance Data", Kenneth R. Lutchen et al., *American Physiological Society*, 1987. pp. 403–413.
"Impact of Frequency Range and Input Impedance on Airway–Tissue Separation Implied From Transfer Impedance", Kenneth R. Lutchen et al., *American Physiological Society*, 1993, pp. 1089–1099.
"Confidence Bounds on Respiratory Mechanical Properties Estimated from Transfer Versus Input Impedance in Human Versus Dogs", Kenneth R. Lutchen et al., *IEEE Transactions on Biomedical Engineering*, vol. 39, No. 6, Jun. 1992, pp. 644–651.
"Inability to Separate Airway from Tissue Properties by Use of Human Respiratory Input Impedance", Kenneth R. Lutchen et al., *American Physiological Society*, 1990, pp. 2403–2412.
"Respiratory Transfer Impedance and Derived Mechanical Properties of Conscious Rats" E. Oostveen et al., *American Physiological Society*, 1992, pp. 1598–1607.
"Mechanical Properties Of The Respiratory System: A Study In Humans And Rats By Forced Oscillations," Comelia Maria Allegonda Oostveen, Sep. 1991, pp. 7–121, 123 and 125.

Primary Examiner—Angela D. Sykes
Assistant Examiner—Stephen Huang
Attorney, Agent, or Firm—Baker & Botts

[57] ABSTRACT

A partial body plethysmograph is provided to enable accurate modeling of a human's respiratory system for input frequencies of up to about 96 Hz using transfer impedance measurements. One preferred embodiment comprises a container for sealingly enclosing a portion of the subject's body, a pressure source for generating pressure signals over a predetermined frequency range, an air flow sensor for measuring the flow of air supplied to the subject, a pressure sensor for measuring the pressure applied to the cavity of the subject and a processor for controlling the pressure source, for storing the measured air flow and pressure and for determining the respiratory system impedance of the subject. An eight element model is used by the processor to inversely model the transfer impedance data and thereby determined characteristics of the respiratory system of the subject.

18 Claims, 7 Drawing Sheets

PARTIAL BODY PLETHYSMOGRAPH FOR MEASURING HUMAN RESPIRATORY SYSTEM IMPEDANCE

BACKGROUND OF THE INVENTION

1. Field of the Invention

This invention relates to plethysmography and forced oscillation respiratory impedance testing of humans to determine respiratory characteristics.

2. Description of the Prior Art

Measurements of human respiratory system impedance using a forced oscillation technique can provide quantitative insight into the mechanical properties of the respiratory system. Typically, the impedance spectra are interpreted using an electromechanical model with proposed physiological parameters. The most widely used electromechanical model is the six-element model proposed by DuBois et al. in 1956 which allows a lumped separation of airways and tissues. DuBois et al. introduced two methods of non-invasively measuring the mechanical properties of the human respiratory system. In one method, small amplitude pressure oscillations are applied at the airway opening (mouth) and the resulting air pressure and air flow at the airway opening are measured. The ratio of the pressure to flow at the airway opening ($P_{ao}/\dot{V}_{ao}$) is termed input impedance ($Z_{in}$). In the second method, the pressure oscillations are applied at the chest wall ($P_{cw}$). The pressure applied to the chest and the air flow at the airway opening ($\dot{V}_{ao}$) are measured. The ratio ($\dot{V}_{ao}$) is termed transfer impedance ($Z_{tr}$).

To analyze respiratory system impedance data, DuBois et al. proposed a three compartment, six element model based on the following assumptions: 1) the lung is a monoalveolar compartment that can be represented by a simple gas compression, 2) the model parameters are frequency independent, and 3) the airways are noncompliant structures. As shown in FIG. 1, this model comprises an airway impedance compartment ($Z_{aw}$) comprising an airways resistance ($R_{aw}$) in series with an airways inertance ($I_{aw}$). The tissue impedance compartment ($Z_{ti}$) is modeled as a tissue resistance ($R_{ti}$) in series with a tissue inertance ($I_{ti}$) and a tissue compliance ($C_{ti}$). These two compartments are separated by a shunt gas compression compartment ($Z_g$) which is modeled as a simple gas compression term ($C_g$).

From this model the transfer impedance ($Z_{tr}$) for the DuBois model is given by Equation 1 below:

$$Z_{tr} = Z_{aw} + Z_{ti} + \frac{Z_{aw} * Z_{ti}}{Z_g} \quad (1)$$

where $$Z_{aw} = R_{aw} + j\omega I_{aw}$$

$$Z_{ti} = R_{ti} + j\omega I_{ti} + \frac{1}{j\omega C_{ti}}$$

and $$Z_g = \frac{1}{j\omega C_g}$$

As Peslin et al. pointed out, though, in using this DuBois model to analyze $Z_{tr}$, it is necessary to independently measure one of the six element parameter values. The most common practice has been to measure functional residual capacity (FRC) and then calculate $C_g$ from Equation 2 below:

$$C_g = \frac{FRC}{P_{ATM} - P_{H_2O}} = \frac{FRC}{969 \text{ cm H}_2\text{O}} \quad (2)$$

wherein $P_{ATM}$=atmospheric pressure (1033 cm H$_2$O) and $P_{H_2O}$=partial pressure of water vapor at 100% saturation (64 cmH$_2$O).

In order to perform transfer impedance testing, Peslin et al. disclosed a body box which completely encloses the subject and provides a tube for connecting the air supply and flow measurement devices to the mouth of the subject inside of the box. Peslin et al. also disclosed the use of a signal generator connected to a loudspeaker to provide the pressure to the subject and a computer to analyze the data collected using a six element model. Because the box entirely encloses the patient, however, some patients were apprehensive about this type of testing.

Most studies of human transfer impedance have been limited to frequency ranges of 4–30 Hz. Others have used frequencies up to 64 Hz.

SUMMARY OF THE INVENTION

It is an object of this invention to provide a system for accurately measuring transfer impedance in humans at frequencies greater than 64 Hz.

It is another object of this invention to develop a structure for measuring transfer impedance in humans which is comfortable, adjustable to users of different sizes and reduces noise due to vibration.

It is a further object of this invention to provide a more accurate model for deriving information from the measurements.

It is still another object of the present invention to provide a method and system for estimating airway properties separate from tissue properties as well as separating airway resistance into central and peripheral components.

It is another object of the present invention to increase the lowest frequency at which standing waves will occur and thereby increase the range of frequencies over which a homogeneous pressure distribution around the chest wall may be determined.

Various embodiments of the present invention are provided. One preferred embodiment comprises a container for sealingly enclosing a portion of the subject's body, a pressure source for generating pressure signals over a predetermined frequency range, an air flow sensor for measuring the amount of air transmitted to the subject, and a pressure sensor for measuring the pressure applied to the thorax of the subject.

A head-out, legs-out plethysmograph according to the present invention allows data to be reliably collected and used for frequency values of up to 96 Hz. Thereby, forced oscillation data may be accurately used with an eight element model of the respiratory system to allow for separation of airway and tissue information, as well as separation of central and peripheral airway information. By providing a system which accurately separates central and peripheral airway information, doctors and technicians may more accurately diagnose the condition of the respiratory function of patients without the need for invasive testing procedures.

Other objects and advantages of the present invention will be apparent when the preferred embodiments of the present invention and the drawings are considered.

DETAILED DESCRIPTION OF THE PREFERRED EMBODIMENTS

Figure 3:
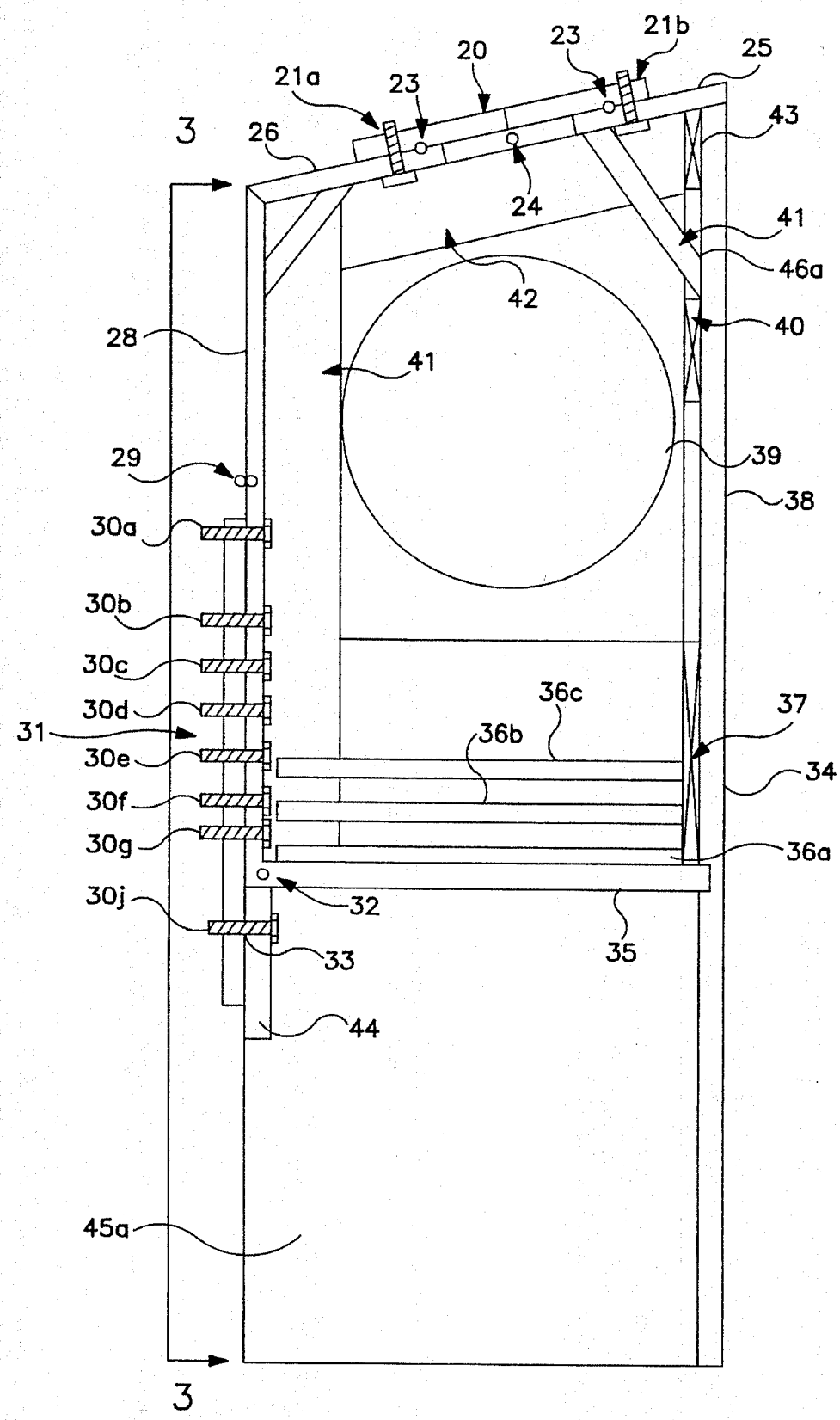
FIG. 3 depicts a cross-sectional side elevation of a partial body plethysmograph according to one preferred embodiment.
Figure 4:
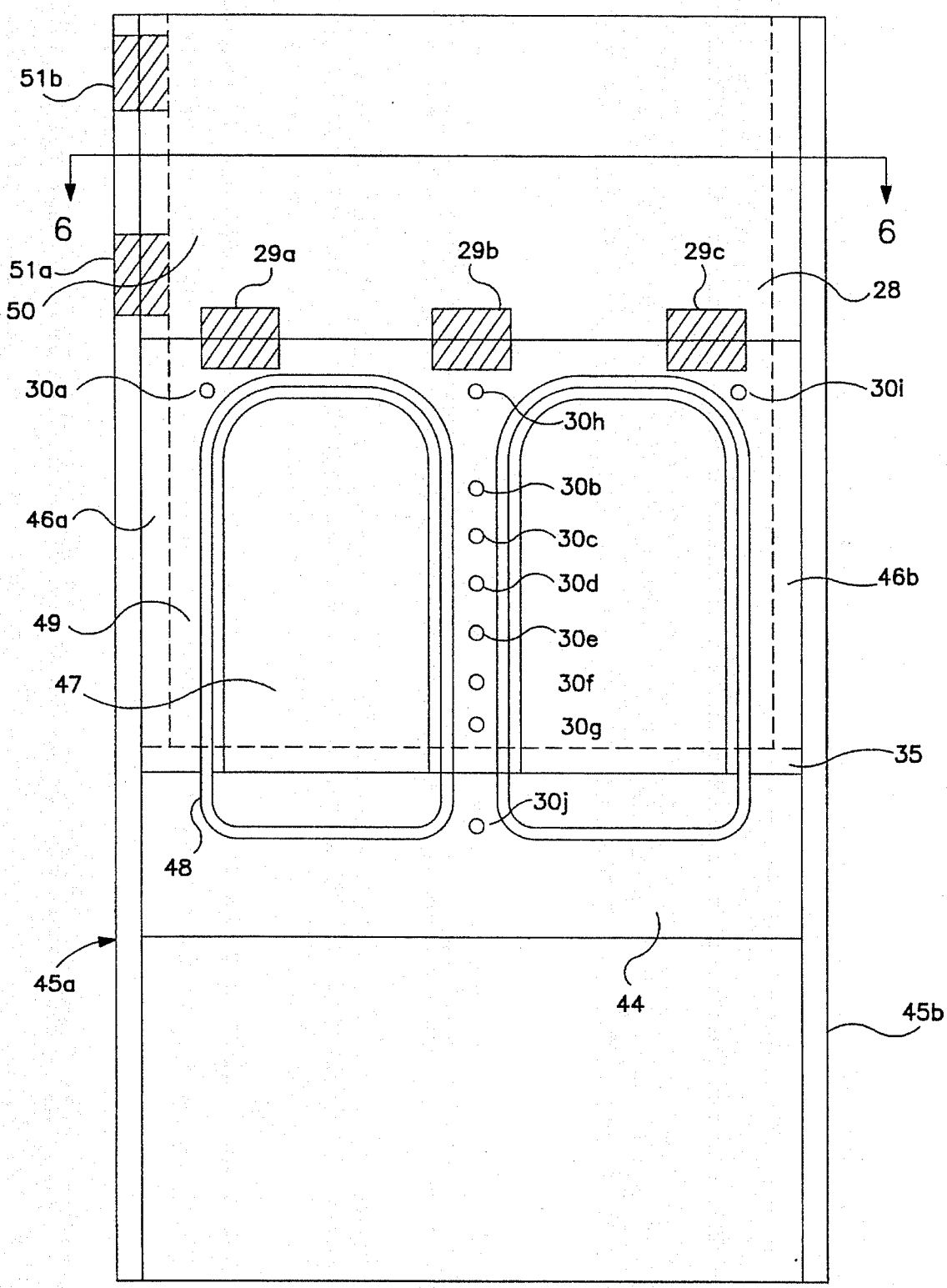
FIG. 4 depicts a frontal elevation of the partial body plethysmograph as seen from 3—3 in FIG. 3.

With reference to FIGS. 3–8, head-out, legs-out plethysmograph 10 will be described. Without limiting the preferred embodiments, some of the elements in the plethysmograph have been described as "front," "back," and "side." As best shown in FIGS. 3–4, the outer surface of the box comprises back wall 34, side walls 45a and 45b, front base 44 and door 28. Back wall 34, side walls 45a and 45b and front base 44 are preferably made of plywood which is preferably about 1 inch thick. The 1 inch thick plywood provides a strong structure and absorbs sound with little vibration. Alternatively, other material may be used, e.g., plexiglass, heavy plastic or the like. Plethysmograph 10 preferably has a bottom portion 35 which attaches between back wall 34 and front base 44. The front edge of bottom portion 35 abuts door 28 when door 28 is closed. To reduce sound loss and to seal plethysmograph 10, tubing 32 is preferably installed in a groove formed along the edge of bottom portion 35. Tubing 32 is preferably seamless latex tubing having a diameter significantly less than the thickness of bottom portion 35, such as a ¼ inch diameter for a 1 inch thick bottom portion. Braces 27, 37, 40, 41, 42, 43 and 46 (FIGS. 3 and 6) may be added to stabilize the structure. These braces are preferably made of 1 inch plywood or similar material suitable for providing stability. In each of side walls 45a and 45b, a speaker hole 39 is preferably disposed for inserting a speaker therethrough. Speaker hole 39 may be any size suitable to fit speakers 6 and 7. Preferably, speaker 6 is mounted to side wall 45a and speaker 7 is mounted to side wall 45b to provide a more uniform sound distribution throughout plethysmograph 10.

Within plethysmograph 10, a plurality of brackets 36 may be provided. For example, brackets 36a, 36b, and 36c may be provided on side wall 45a whereas brackets 36d, 36e and 36f may be provided on side wall 45b. Additionally, brackets 36a and 36d may be positioned substantially parallel to form a lowest seat setting. Similarly, brackets 36b and 36d may be positioned to form a medium setting and brackets 36c and 36f (FIG. 6) may be positioned to form a highest seat setting. A seat (not shown) may then be placed on appropriate brackets so that the distance between the seat and the top of plethysmograph 10 substantially corresponds to the torso height of the subject to be tested. For example, by placing the seat on brackets 36c and 36f a subject having a relatively short torso may be accommodated; whereas, by placing the seat on brackets 36a and 36d, a subject having a relatively tall torso may be accommodated. The seat used in plethysmograph 10 preferably includes a layer of vibration insulation, e.g., foam rubber or the like, to assist in reducing noise. The seat may be constructed of, for example, plywood or plastic or the like.

Preferably, the distances between the various brackets and the top of the plethysmograph are selected to accommodate a wide range of torso heights. For example, the plethysmograph may be designed to accommodate 90 percent of all adult humans. By using anthropometric data regarding both male and female humans, the distance from the brackets to the top of the plethysmograph may be selected to accommodate the desired range of adult humans. Sample shoulder to seat height dimensions measured for the 5th percentile and 95th percentile adult humans are depicted in Table 1 below for both males and females.

| SEX | 5th percentile | 95th percentile |
|---|---|---|
| Male | 22.5 inches | 26.6 inches |
| Female | 21.2 inches | 24.6 inches |

Table 1: Shoulder to seat height data for adult humans

Using three brackets, for example, the distance between the brackets and the top of the plethysmograph may be selected to be as depicted in Table 2 below. Other distances may alternatively be selected. Additionally, the number of brackets used may be varied to provide either fewer or more seat positions. It should also be understood that a plethysmograph which accommodates a wider range of adult humans may also be desired to take into consideration even the 100th percentile adult human.

| Brackets | Distance from brackets to top of plethysmograph |
|---|---|
| 36a–36c | 28.00 inches |
| 36b–36d | 25.50 inches |
| 36c–36e | 22.75 inches |

Table 2: Bracket to top of plethysmograph seat distance options

Attached to door 28 and front base 44 are a plurality of fasteners 30a–30j. Fasteners 30a–30j may be any type of fastening device suitable for securing leg plate 31 to door 28 and front base 44. Fasteners 30a–30j preferably are nuts and bolts arranged so that the nuts (not shown) are affixed outside of leg plate 31. Other types of fasteners 30a–30j may also be employed. Additionally, the number of fasteners may be increased or decreased as desired to suit the particular door and front base arrangement.

Figure 5A:
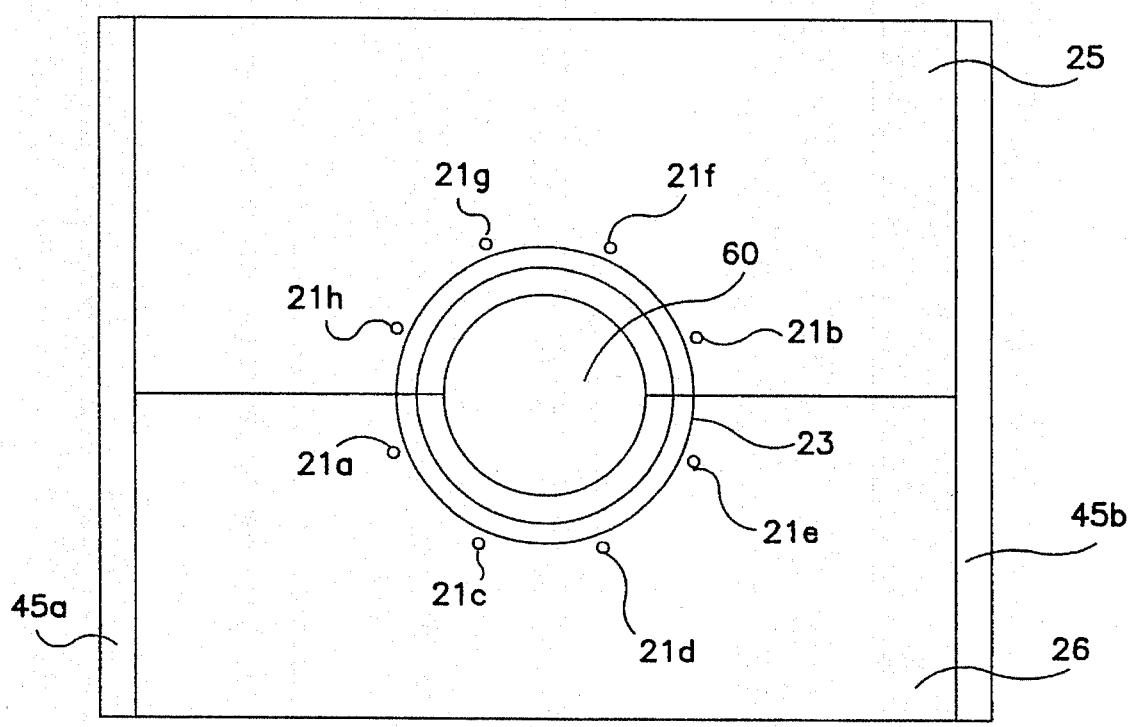
FIG. 5a depicts a top plan view of the partial body plethysmograph of FIG. 3.

As best seen in FIGS. 3 and 5a, the top of plethysmograph 10 comprises back top portion 25 and front top portion 26. The top may alternatively be formed by a single top portion. Affixed to top portions 25, 26 are fasteners 21a–21h (FIG. 5a) which may comprise bolts or other fastening devices. Fasteners 21a–21h cooperate with holes 71a–71h on head plate 20 to secure head plate 20 to top portions 25, 26. Tubing 23 may be positioned within shallow grooves formed in top portions 25, 26 to seal the mating surfaces between top portions 25, 26 and head plate 20. The top of plethysmograph 10 is preferably disposed at an angle with respect to bottom portion 35. Normal forward inclination of the axis through the human head from a vertical axis which respect to the ground for most humans is about 10°–15°. Therefore, the top is preferably inclined at an angle of about 12.5° from front to back as depicted in FIG. 3. This configuration is more comfortable for a subject when the subject is positioned in plethysmograph 10 with his or her head extending through head opening 60. Head opening 60 is preferably large enough to allow a human head to pass therethrough, for example, about 9 inches in diameter.

Hinges (not shown) may be installed whereby top portions 25 and 26 may each be swung upward and away from plethysmograph 10. Alternatively, front top portion 26 may be attached to door 28 using brace 27 (FIG. 3) or some other mechanism so that when door 28 swings open, front top portion 26 also opens. This arrangement of front top portion 26 and door 28 allows the subject to place his or her neck into an enlarged head opening 60. As such, top portions 25 and 26 operate as a yoke so that head opening 60 need only be large enough to permit a human neck to fit therethrough. After the subject places his head in the enlarged head opening 60, door 28 may be closed and correspondingly front top portion 26 closes around the subject's neck. Head opening 60 need then only have a diameter of about 6 inches, or approximately the diameter of the 95th percentile adult human neck, when top portions 25 and 26 operate as a yoke.

Figure 5B:
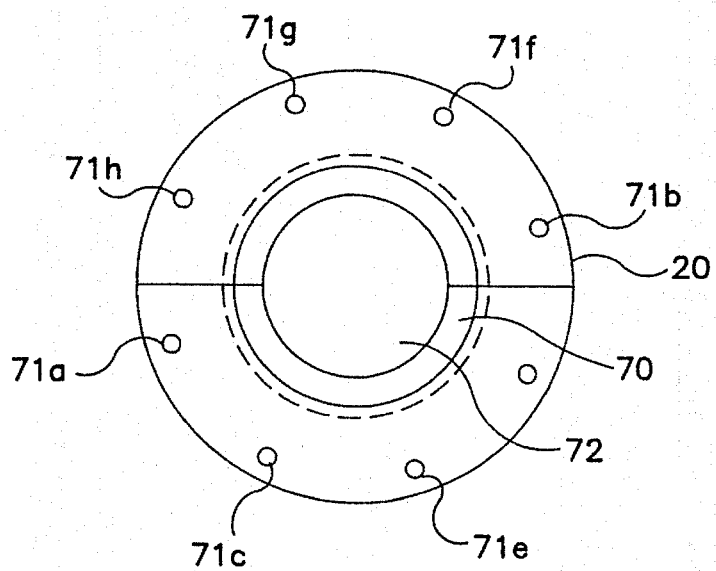
FIG. 5b depicts a head plate of the partial body plethysmograph according to one preferred embodiment.

With reference to FIG. 5b, head plate 20 is preferably comprised of two semicircular portions which form a yoke to fit around a human neck. Opening 72 in head plate 20 is formed by the two semicircle portions. Surrounding the inside of the two semicircle portions is cushion material 70 which is preferably soft foam rubber or the like which may be glued or otherwise affixed to the semicircle portions of the two halves of head plate 20. Other soft materials may additionally or alternatively be used. A plurality of head plates 20 may be provided, each head plate having a different inner diameter of opening 72. For example, one head plate 20 may have an opening 72 with an inner diameter of 5 inches while another may have an inner diameter of 6 inches. The inner diameter of head plate 20 may be then selected to fit the size of the neck of the subject to be placed in plethysmograph 10 for testing. Head plate 20 is also provided with a plurality of fastener holes 71a–71h which cooperate with fasteners 31a–31h on top portions 25 and 26. Nuts or other securing devices may be placed over the head plate 20 for securing head plate 20 to top portions 25 and 26.

Figure 6:
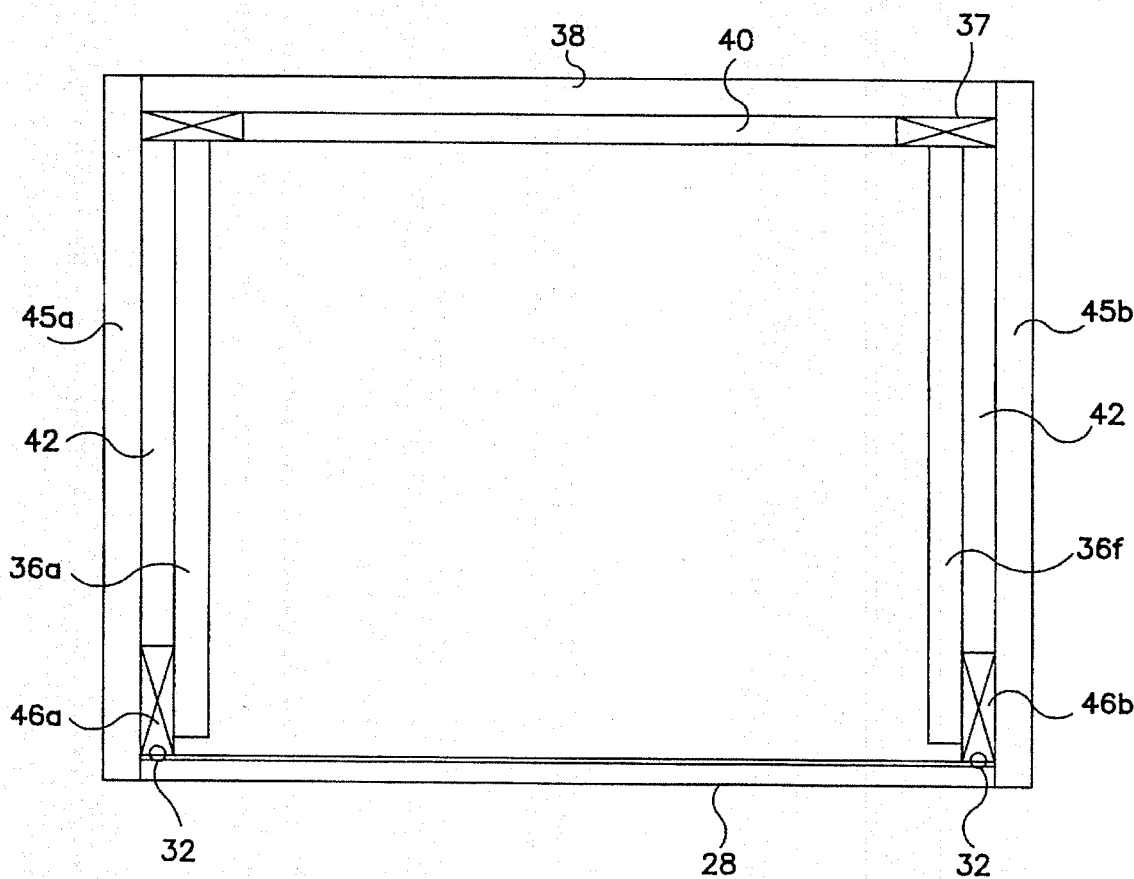
FIG. 6 depicts a cross sectional view of the partial body plethysmograph taken along 6—6 in FIG. 4.

Turning to FIG. 4, the front of plethysmograph 10 is depicted. Door 28 includes a top door portion 50 and a bottom door portion 49 attached via hinges 29a–29c. Hinges 29a–29c allow bottom door portion 49 to swing open in a direction away from plethysmograph 10. Bottom door portion 49 comprises two leg openings 47 through which the subject's legs may pass when seated in plethysmograph 10. Alternatively, plethysmograph 10 may have a solid front, whereby the patient's legs may be contained within plethysmograph 10. If leg openings are used, tubing 48 is provided around the leg openings 47 to seal the mating surfaces between leg plate 31 (FIGS. 7 and 8) and bottom door portion 49. Tubing 48 may additionally extend into front base 44 since leg plate 31 preferably fits over front base 44 as well. Further, as seen in FIG. 6, tubing 32 may be provided in shallow grooves formed in braces 46a and 46b to form a seal when door 28 is closed and thereby abuts bottom portion 35. Door 28 is attached to side wall 45a by hinges 51a, 51b and may be secured to side wall 45b by a latch (not shown) or any other type of device for temporarily securing door 28 to side wall 45b.

Figure 7:
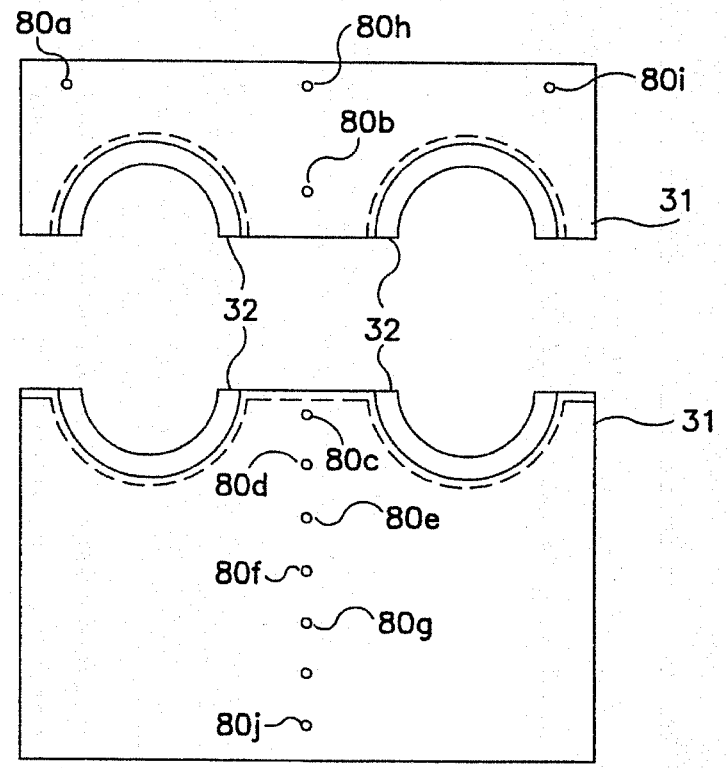
FIGS. 7 and 8 depict leg plates according to two preferred embodiments.
Figure 8:
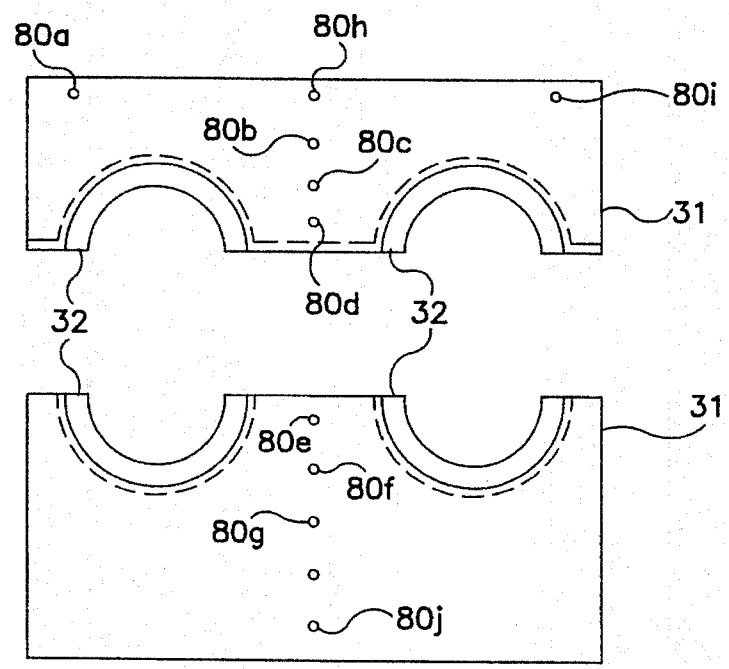

FIGS. 7 and 8 depict two embodiments of leg plate 31. FIG. 7 depicts a leg plate 31 for use when the seat is set at a high setting such as on brackets 36c and 36f. FIG. 8 depicts a leg plate 31 for use when the seat is set for a medium setting such as on brackets 36b and 36e. Each of leg plates 31 is provided with a plurality of bolt holes 80 each corresponding to a bolt 30 on door 28. Additionally, two leg openings are formed by two semicircles in the two sections of leg plate 31. The leg openings may be provided with cushion material 32 which is preferably foam rubber or the like for providing a comfortable, yet snug fit of the leg plates around the legs of the subject.

As will be readily appreciated, the components of plethysmograph 10 secure the torso of a subject within a substantially airtight environment. By providing a plurality of braces, the stability of plethysmograph 10 is increased. Consequently, plethysmograph 10 is stable, vibration is minimized, and the purity of the sound directed to the subject in plethysmograph 10 is maximized, which in turn increases the accuracy of the data collected during testing. Further, by reducing the volume of the chamber which surrounds the subject's chest during testing, a wider range of pressure signal frequencies is permitted. The reduced volume increases the frequency at which standing waves first occur. Because standing waves occur at a higher frequency, vibration correspondingly does not occur until a much higher frequency. Therefore, the range of frequencies over which homogeneous pressure distribution around the chest may be claimed without undue interference from vibration is increased. The range of reliable frequencies is extended to at least 96 Hz according to the preferred embodiments.

Figure 1:
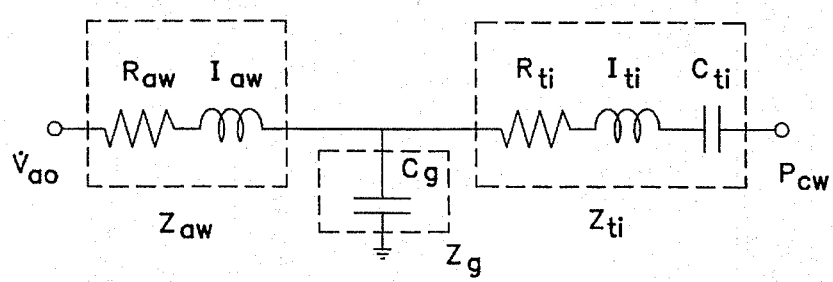
FIG. 1 depicts a six element model of the respiratory system according to the prior art.
Figure 2:
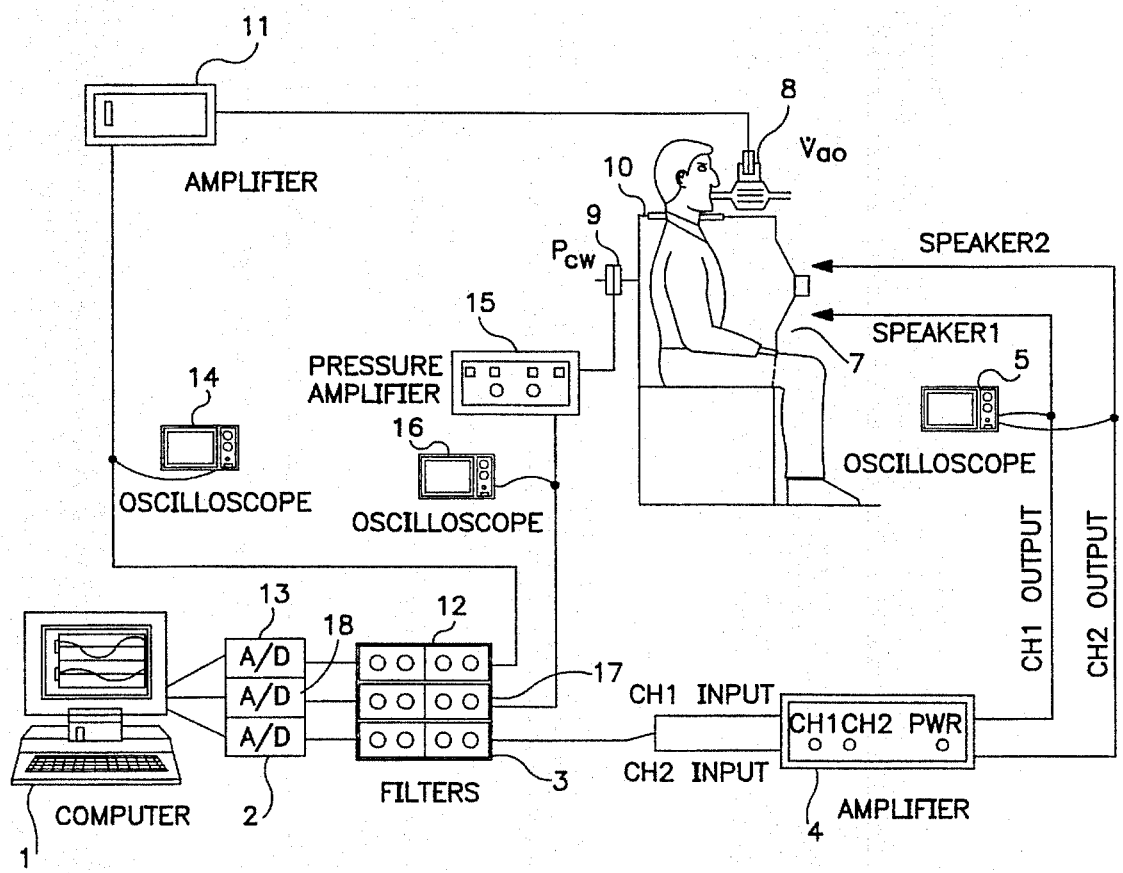
FIG. 2 depicts a system for measuring transfer impedance in humans according to one preferred embodiment.

With reference to FIG. 2, there is shown a system for measuring transfer impedance comprising head-out, legs-out plethysmograph 10 and a differential pressure transducer 8 which is inserted into the subject's mouth. Differential pressure transducer 8 is connected via a pneumotachometer (not shown) to signal amplifier 11. Signal amplifier 11 is connected via band-pass filter 12 and A/D converter 13 to computer 1. Also attached to plethysmograph 10 is a pressure transducer 9, which, in turn, is connected to pressure amplifier 15. Pressure amplifier 15 is connected to computer 1 via band-pass filter 17 and A/D converter 18.

Pressure input to the subject may be achieved via speakers 6 and 7. Computer 1 is connected via D/A converter 2 and band-pass filter 3 to a dual-channel stereo amplifier 4. Stereo amplifier 4 transmits output signals to speakers 6 and 7.

Signal input to the subject is achieved via computer 1, amplifier 4 and speakers 6 and 7. A pseudo random noise signal (PRN) is generated by computer 1. Computer 1 may be any computer or processor capable of transmitting data at a rate sufficient to provide digital information to D/A converter 2 such that D/A converter 2 may generate analog signals from about 0.1 to 128 Hz in appropriate intervals, for example, 2 Hz intervals and analyzing data which is collected. A Gateway 2000 386/25 computer, for example, may be used. Computer 1 preferably provides data at a rate of at least twice the highest frequency analog signal to be generated. Hence, a data rate of about 512 Hz, for example may be used, which is well above twice 128 Hz. A slower data rate may be used down to a minimum of 256 Hz. Digital data is transmitted from computer 1 to D/A converter 2 and then to band-pass filter 3. Band-pass filter 3 preferably eliminates the DC (0 Hz) component and high frequency harmonics such as through a band-pass range of about 0.5 Hz to 160 Hz.

Band-pass filter 3 may be any type of analog band pass filter, such as an Ithaco model 4113, for example. The output of band-pass filter 3 is sent to the two channels of stereo amplifier 4. To ensure that the two channels of stereo amplifier 4 are evenly matched, an oscilloscope 5 may be used. Such signal matching techniques using oscilloscopes are well known. Each signal output from band-pass filter 3 is then amplified and provided to one of speakers 6 and 7. Amplifier 4 may be any type of amplifier, such as a Crown, model D150A, for example. Speakers 6 and 7 may be any type of speaker having a frequency response sufficient to distinguish between frequencies in the low range (2 to 128 Hz) being transmitted, such as a Pyle 15 inch Professional High Fidelity Woofer, part number W 1560, for example, which has a frequency response of 20–3000 Hz.

As an alternative embodiment, instead of two speakers 6 and 7, only one speaker could be used. When using one speaker, a one-channel amplifier may be used in place of stereo amplifier 4. When two speakers are used, testing is preferably performed to ensure that the speaker cones of speakers 6 and 7 move synchronously. If each of the two cones of speakers 6 and 7 do not move into and out of plethysmograph 10 simultaneously, the net volume change in the chamber will be less than expected, and thus the test results will be inaccurate. To ensure synchronicity of speakers 6 and 7, an accelerometer (not shown) may be used. It should be recognized that methods for ensuring synchronicity of two speakers are within the skill of one of ordinary skill in the art and many variations on performing this process may be used.

The data collection systems will hereinafter be described. Air is supplied to the subject through differential pressure transducer 8. Differential pressure transducer 8 may be any type of differential pressure transducer such as a Celsco, model LCVR, 0–2 cm $H_2O$, for example. Differential pressure transducer 8 is mounted across a pneumotachometer (not shown) such as a Fleisch No. 2, for example. The pneumotachometer produces analog signals representative of changes in air flow supplied to the subject's mouth for transmission to amplifier 11. Other devices and methods of gathering air flow data may also be used.

Amplifier 11 receives the analog signals from the pneumotachometer and amplifies those signals. Amplifier 11 may be any type of analog amplifier, such as a Phillips PM 5171 amplifier, for example. Amplifier 11 transmits this amplified signal to band pass filter 12 which preferably has a band pass range of between about 0.8 Hz and about 160 Hz. An Ithaco, model 4113, for example may be used as band pass filter 12. Band-pass filter 12 preferably filters frequencies above 0.5 Hz, which is approximately the frequency of the breathing cycle, and below 160 Hz to filter out high frequency noise. A/D converter 13 samples the analog output of band-pass filter 15 at about 512 Hz and transmits this digital data to computer 1 for processing and subsequent analysis.

Pressure data is collected primarily via pressure transducer 9. Pressure transducer 9 may be any type of pressure transducer such as a Microswitch brand, for example. Pressure transducer 9 is preferably placed on a heavily braced portion of plethysmograph 10 to reduce vibrations transmitted to the transducer. The location of pressure transducer 9, however, with respect to plethysmograph 10 is irrelevant due to the homogeneity of pressure within plethysmograph 10 created by utilizing two speakers 6 and 7. The pressure signal from pressure transducer 9 is transmitted to pressure amplifier 15 which amplifies the signal before passing it to band-pass filter 17. Band-pass filter 17, like band-pass filter 12, filters out high frequencies and passes a frequency band from about 0.8 Hz to about 160 Hz. Band-pass filter 17 may be any analog band-pass filter, such as an Ithaco, model 4113, for example. A/D converter 18 samples the data at about 512 Hz and transmits this data to computer 1 for storage and subsequent analysis. Differential pressure transducer 8 and pressure transducer 9 are preferably digitally matched according to known techniques. Air flow and pressure amplifier gains may be checked via oscilloscopes 14 and 16 before each subject is tested to ensure consistency with previous settings. Also, oscilloscope 5 may be used to ensure matching of the amplitudes of the output signals from amplifier 4 to speakers 6 and 7. The gain of the power amplifier is preferably adjusted so that the highest pressure delivery to plethysmograph 10 is obtained while ensuring that the speaker cones still move in approximately a sinusoidal fashion at even the lowest frequency. Adjustments are also preferably made to ensure that the sound level is comfortable for the subject being tested, that the box vibrations caused by the high volume are minimized and that the pressure inside the box does not exceed the measurement range of pressure transducers 8 and 9.

Operation of the data collection and analysis method will now be described. Due to the structural stability and noise reduction provided by the preferred embodiments, data from about 2 to about 128 Hz may be transmitted and collected. A pseudo random noise (PRN) signal with a frequency content from about 2 to about 128 Hz in about 2 Hz increments is used and sent by computer 1 to D/A converter 2. As noted above, the frequency response of speakers 6 and 7 as used in this example, is only about 20–3000 Hz. Therefore, the low end of the signal (2–32 Hz) is preferably enhanced to improve the performance of the speakers through amplifier 4. The high end of the signal (80–128 Hz) may also be enhanced to improve the signal to noise ratio by increasing the applied pressure and resulting flow at those frequencies. Techniques for enhancing the lower frequencies are known in the art. A technique for minimizing the crest factor (difference between the maximum and minimum peaks) of the PRN signal divided by a term related to the total energy in the signal is also preferably performed. Such techniques are also well known in the art from the teaching of Van der Ouderaa et al.

After collection of data generated at these frequency ranges, a gradient optimization technique, which minimizes the square of the difference between measured data and model impedance values, is used. The performance index of the gradient optimization technique is given by Equation 3 below:

$$P.I. = \frac{\sum_{i=1}^{N} |Z_{tr_d}(i) - Z_{tr_m}(i)|^2}{|Z_{tr_d}|^2} \qquad (3)$$

where $Z_{tr_d}(i)$ is the $i^{th}$ measured impedance data point and $Z_{tr_m}$ is the $i^{th}$ predicted impedance data point.

The quality of the model fit to the data ($S^2$) is determined by Equation 4 below:

$$S^2 = \frac{P.I.}{(n-P)} \qquad (4)$$

where n is the number of data points fit and P is the number of parameters. As S decreases, data more accurately fits the expected value for the subject.

Figure 9:
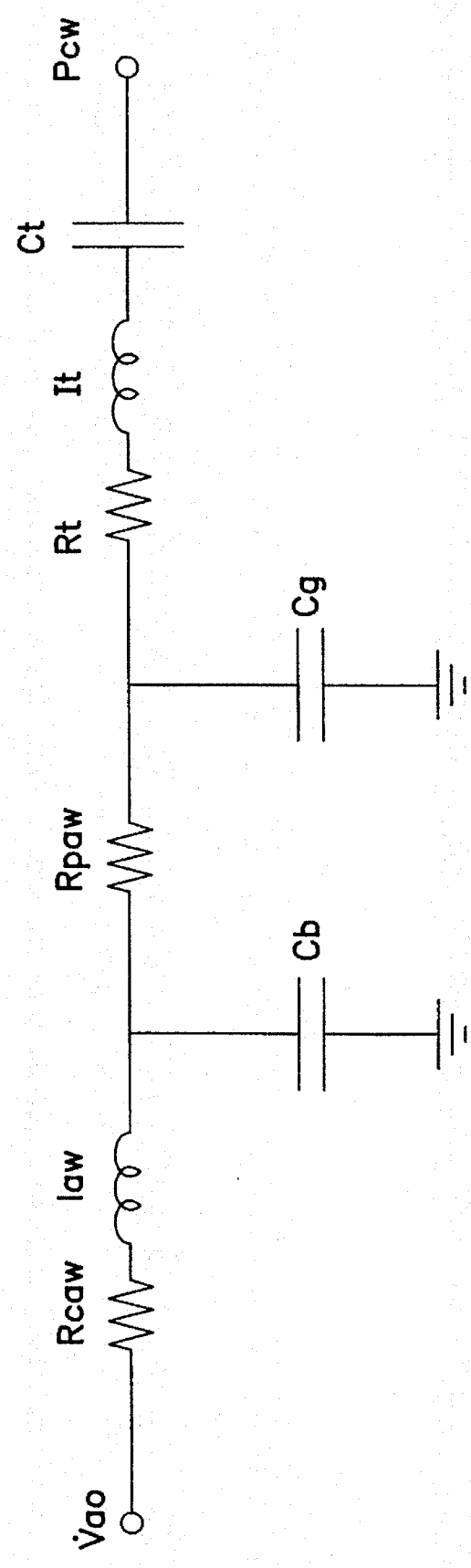
FIG. 9 depicts an eight element model of the respiratory system for use according to the preferred embodiment.

With reference to FIG. 9, an eight element model is employed to inversely model the data collected for $Z_{tr}$ into the various components of the model. Simple gas compression, $C_g$, may be estimated according to one of the many techniques such as open-circuit multi-breath nitrogen washout, closed-circuit multibreath helium dilution, and body plethysmography, for example. $C_g$ is set as a constant according to one of the measurement techniques as described. $C_b$ represents a shunt pathway corresponding to the lumped bronchial airway wall compliance of the subject and separates the airway compartment into central and peripheral resistance. Since the vast majority of inertance of humans occurs in the trachea, all airway inertance is modeled in the central airway branch where the trachea is located. $R_{caw}$ represents the resistance of the central airways and $R_{paw}$ represents the resistance of the peripheral airways. $I_{aw}$, $R_t$, $I_t$, and $C_t$ correspond to inertance of the airways, resistance of the tissue, inertance of the tissue and compliance of the tissue, respectively.

This eight element model is used for interpreting the $Z_{tr}$ data collected. By inversely modeling the $Z_{tr}$ data gathered over the frequency range from about 2 Hz to about 96 Hz, and comparing the determined model values with expected model values, potential sources of disease or malfunction of the respiratory system may be determined. For example, an increase in the inversely modeled data collected for $R_{aw}$ (either $R_{caw}$ or $R_{paw}$) as compared to a predetermined expected value for a subject having similar physical conditions may indicate an airflow obstruction. Such an obstruction may be indicative of an obstructive disease such as asthma, chronic bronchitis or emphysema, for example. This method of comparison of data collected and fit into the eight element model with an expected eight element model enables fast and non-intrusive means of determining patient respiratory characteristics.

Because of the design of the head-out, legs-out plethysmograph of the present invention, data may be reliably collected and used at frequencies up to about 96 Hz. This range of frequencies is even larger than necessary to effectively utilize the eight element model. Therefore, if desired, a smaller range of frequencies may be employed. The structure of the plethysmograph provides an increase in the reliable frequency range for $Z_{tr}$ forced oscillation data and facilitates the use of an eight element model which provides more insight into the operation of the respiratory system. This eight element model allows for separation of airway and tissue information as well as separation of data regarding the airways into its central and peripheral airway components. The increased accuracy and specificity of the data gathered enables doctors and technicians to diagnose patients without the use of invasive procedures on the patient.

Further, the time required to perform these tests is usually only about 6 minutes. The relatively short time of the test helps to reduce the stress often caused by other methods of respiratory testing. Also, because the present invention allows for at least the head and potentially also the legs of the patient to be outside of the plethysmograph, the patient will likely feel less confined. The head-out, legs-out structure also allows the doctor to more easily communicate with the patient and observe the patient during the testing. The adjustability of the present invention increases the comfort of this box and allows one device to be used for a wide range of adult patients.

Although a detailed description of the invention has been provided, it should be understood that the scope of the invention is not to be limited thereby, but is to be determined by the claims which follow. Various modifications and alternatives will be readily apparent to one of ordinary skill in the art.

What is claimed is:

1. An apparatus for analyzing a respiratory system of a subject, having a body, a neck, legs, and a respiratory system impedance and being supplied with a flow of air, comprising:

a container for enclosing a portion of the subject's body, said container comprising a chamber portion and a neck opening for the subject's neck, whereby a pressure is applied to the portion of the subject's body enclosed in the chamber;

a pressure source for generating pressure signals within the container over a predetermined frequency range, wherein the pressure signals vary the pressure applied to the portion of the subject enclosed in the chamber and comprises pseudo random noise signals having frequency components from about 0.1 Hz to about 128 Hz in about 2 Hz increments;

an air flow sensor for measuring the flow of air supplied to the subject and providing a measured air flow value;

a pressure sensor for measuring the pressure applied to the portion of the subject's body enclosed within said container and providing a measured pressure value; and a processor connected to said air flow sensor, said pressure sensor and said pressure source, said processor operative to control said pressure source, store the measured air flow value and the measured pressure value, determine the respiratory system impedance of the subject using the measured air flow value and the measured pressure value and generate an eight element model of the subject's respiratory system by inversely modeling the respiratory system impedance.

2. The apparatus of claim 1 wherein said air flow sensor comprises a differential pressure transducer.

3. The apparatus of claim 1 wherein said pressure sensor comprises a pressure transducer.

4. The apparatus of claim 1 wherein the subject's respiratory system comprises central airways, peripheral airways, lumped bronchial airway walls and tissue, wherein the subject has an alveolar gas compression value associated therewith, wherein the central airways have a resistance and an inertance associated therewith, wherein the peripheral airways have a resistance associated therewith, wherein the lumped bronchial airway walls have a compliance associated therewith, wherein the tissue has a resistance, an inertance and a capacitance associated therewith and wherein said eight element model comprises:

a resistance corresponding to the resistance of the central airways of the subject;

an inductance corresponding to the inertance of the central airways of the subject;

a resistance corresponding to the resistance of the peripheral airways of the subject;

a capacitance corresponding to the compliance of the lumped bronchial airway walls of the subject having one terminal connected to ground;

a capacitance corresponding to the alveolar gas compression value of the subject;

a resistance corresponding to the resistance of the tissue of the subject;

an inductance corresponding to the inertance of the tissue of the subject; and a capacitance corresponding to the compliance of the tissue of the subject.

5. The apparatus of claim 1 further comprising a processor for inversely modeling the respiratory system impedance using data collected at frequencies from about 0.1 Hz to about 96 Hz.

6. The apparatus of claim 1 further comprising:

braces connected to said container for reducing vibration of said container caused by the pressure source signals; and sealing means for sealing said container around the subject's neck.

7. The apparatus of claim 1 wherein said container comprises a seat portion, three wall portions, a door portion, a plurality of seat brackets and a top portion, wherein said seat portion rests on at least two of said seat brackets and wherein said seat portion and said top portion are separated by a distance which may be adjusted by resting said seat portion on different seat brackets.

8. The apparatus of claim 7 wherein said top portion and said seat portion are angularly disposed with respect to each other.

9. The apparatus of claim 1 wherein said container further comprising at least one leg opening for the subject's legs and sealing means for sealing said container around the subject's legs.

10. A method of evaluating a respiratory system of a subject, having a body, a neck, legs, and a respiratory system impedance and being supplied with a flow of aft, comprising the steps of:

enclosing a portion of the subject's body within a container, whereby an air pressure is applied to the portion of the subject enclosed in the chamber and wherein the portion comprises the subject's body below the subject's neck;

applying pressure signals to the subject within the container, wherein the pressure signals vary the air pressure applied to the portion of the subject enclosed in the chamber;

measuring the flow of air supplied to the subject;

measuring the air pressure within the container;

determining respiratory system impedance data for the subject using the measured air flow and air pressure; and inversely modeling the respiratory system impedance data into an eight element model using data for input frequencies from about 0.1 Hz to about 9.6 Hz.

11. The method of claim 10 further comprising the step of enclosing the subject's body above the subject's legs within the container.

12. The method of claim 10 further comprising the step of comparing each element of said eight element model with predetermined respiratory system data.

13. The method of claim 10 further comprising the step of stabilizing the container with braces.

14. The method of claim 10 wherein the subject's respiratory system comprises central airways, peripheral airways, lumped bronchial airway walls and tissue, wherein the subject has an alveolar gas compression value associated therewith, wherein the central airways have a resistance and an inertance associated therewith, wherein the peripheral airways have a resistance associated therewith, wherein the lumped bronchial airway walls have a compliance associated therewith, wherein the tissue has a resistance, an inertance and a capacitance associated therewith and wherein said eight element model comprises:

a resistance corresponding to the resistance of the central airways of the subject;

an inductance corresponding to the inertance of the central airways of the subject;

a resistance corresponding to the resistance of the peripheral airways of the subject;

a capacitance corresponding to the compliance of the lumped bronchial airway walls of the subject having one terminal connected to ground;

a capacitance corresponding to the alveolar gas compression of the subject;

a resistance corresponding to the resistance of the tissue of the subject;

an inductance corresponding to the inertance of the tissue of the subject; and a capacitance corresponding to the compliance of the tissue of the subject.

15. A method of evaluating a subject, having a body, a neck, legs, and a respiratory system impedance and being supplied with a flow of air, comprising the steps of:

enclosing a portion of the subject's body within a container, said container comprising a chamber portion and a neck opening for the subject's neck whereby an air pressure is applied to the portion of the subject enclosed in the chamber and wherein the portion comprises the subject's body below the subject's neck;

applying pressure signals to the subject within the container, using at least two speakers wherein the pressure signals vary the pressure applied to the portion of the subject enclosed in the chamber;

measuring the flow of air supplied to the subject;

measuring the air pressure within the container;

determining respiratory system impedance data for the subject using the measured air flow and air pressure; and inversely modeling the respiratory system impedance data into an eight element model.

16. A method of evaluating a respiratory system of a subject, having a body, a neck, legs, and a respiratory system impedance and being supplied with a flow of air, comprising the steps of:

enclosing a portion of the subject's body within a container, said container comprising a chamber portion and a neck opening for the subject's neck whereby an air pressure is applied to the portion of the subject enclosed in the chamber and wherein the portion comprises the subject's body below the subject's neck;

applying pressure signals to the subject within the container wherein the pressure signals vary the air pressure applied to the portion of the subject enclosed in the chamber and wherein the pressure signals comprise pseudo random noise signals having frequency components from about 0.1 Hz to about 128 Hz in about 2 Hz increments;

measuring the flow of air supplied to the subject;

measuring the air pressure within the container;

determining respirator system impedance data for the subject using the measured air flow and air pressure; and inversely modeling the respiratory system impedance data into an eight element model.

17. An apparatus for analyzing a respiratory system of a subject, having a body, a neck, legs, and a respiratory system impedance and being supplied with a flow of air, comprising:

a container for enclosing a portion of the subject's body, said container comprising a chamber portion and a neck opening for the subject's neck, whereby a pressure is applied to the portion of the subject's body enclosed in the chamber;

a pressure source comprising at least two speakers for generating pressure signals within the container over a predetermined frequency range, wherein the pressure signals vary the pressure applied to the portion of the subject enclosed in the chamber;

an air flow sensor for measuring the flow of air supplied to the subject and providing a measured air flow value;

a pressure sensor for measuring the pressure applied to the portion of the subject's body enclosed within said container and providing a measured pressure value and a processor connected to said air flow sensor, said pressure sensor and said pressure source, said processor operative to control said pressure source, store the measured air flow value and the measured pressure value, determine the respiratory system impedance of the subject using the measured air flow value and the measured pressure value and generate an eight element model of the subject's respiratory system by inversely modeling the respiratory system impedance.

18. The apparatus of claim 17 further comprising a processor for inversely modeling the respiratory system impedance using data collected at frequencies from about 0.1 Hz to about 96 Hz.

* * * * *